United States Patent
Johannessen

(10) Patent No.: US 8,539,822 B2
(45) Date of Patent: Sep. 24, 2013

(54) APPARATUS AND METHOD FOR MEASURING AUGMENTED OSMOTIC PRESSURE IN A REFERENCE CAVITY

(75) Inventor: Erik Johannessen, Horten (NO)

(73) Assignee: Lifecare AS, Bergen (NO)

(*) Notice: Subject to any disclaimer, the term of this patent is extended or adjusted under 35 U.S.C. 154(b) by 738 days.

(21) Appl. No.: 12/733,258

(22) PCT Filed: Aug. 20, 2008

(86) PCT No.: PCT/NO2008/000295
§ 371 (c)(1),
(2), (4) Date: Apr. 21, 2010

(87) PCT Pub. No.: WO2009/025563
PCT Pub. Date: Feb. 26, 2009

(65) Prior Publication Data
US 2010/0223981 A1  Sep. 9, 2010

(30) Foreign Application Priority Data
Aug. 20, 2007  (NO) .................................. 20074244

(51) Int. Cl.
*G01N 13/04* (2006.01)
(52) U.S. Cl.
USPC ...... 73/64.47; 422/68.1; 422/82.02; 436/148; 600/309; 600/311; 600/316; 600/365
(58) Field of Classification Search
USPC ...... 73/64.47; 422/62, 68.1, 68.13; 436/148; 600/309, 311, 316, 365
See application file for complete search history.

(56) References Cited

U.S. PATENT DOCUMENTS

| 3,628,373 | A | * | 12/1971 | Gilbert | 73/64.47 |
| 3,635,075 | A | * | 1/1972 | Gilbert | 73/64.47 |
| 4,028,931 | A | * | 6/1977 | Bisera et al. | 73/64.47 |
| 4,538,616 | A | | 9/1985 | Rogoff | 128/632 |
| 4,822,336 | A | | 4/1989 | DiTraglia | 604/50 |
| 5,337,747 | A | * | 8/1994 | Neftel | 600/347 |
| 6,224,550 | B1 | | 5/2001 | Ellingsen | 600/366 |
| 6,268,161 | B1 | * | 7/2001 | Han et al. | 435/14 |
| 6,926,670 | B2 | * | 8/2005 | Rich et al. | 600/459 |
| 7,276,028 | B2 | * | 10/2007 | Ellingsen et al. | 600/309 |
| 7,490,522 | B2 | * | 2/2009 | Ruehrig et al. | 73/862.335 |

(Continued)

FOREIGN PATENT DOCUMENTS

DE  2146613 A1  3/1973

*Primary Examiner* — Hezron E Williams
*Assistant Examiner* — Hoang Nguyen
(74) *Attorney, Agent, or Firm* — Steptoe & Johnson LLP

(57) ABSTRACT

An apparatus and method for measuring augmented osmotic pressure in a reference cavity is provided, in which the device comprise a substrate frame (4) attached to a support structure (1) in which a plurality of transducer devices (2) are buried. An array of osmotic membranes (3) is integrated by the support structure and which acts to facilitate a trans-membrane pressure gradient as a function of the osmotic pressure change in a sealed cavity (7). The sealed cavity is formed by rigid substrate materials (5,6) in which the membranes, support structure and transducer devices only will be subject to induced stress in response to augmented osmotic pressure and thereby generate a pressure induced signal change observed from the transducer devices. The transducer devices may be arranged as piezoresistive elements, as micromechanical switches, as variable capacitive elements or as an optical light source and detector. The device can be used to monitor changes in osmotic pressure in response to a concentration change of a specified dissolved solute particle.

31 Claims, 5 Drawing Sheets

(56) References Cited

U.S. PATENT DOCUMENTS

| | | | |
|---|---|---|---|
| 7,553,669 B2 * | 6/2009 | Torres et al. | 436/34 |
| 7,657,297 B2 * | 2/2010 | Simpson et al. | 600/347 |
| 7,790,111 B2 * | 9/2010 | Torres et al. | 422/82.02 |
| 2002/0151816 A1 * | 10/2002 | Rich et al. | 600/547 |
| 2005/0136544 A1 | 6/2005 | Torres et al. | 436/34 |
| 2005/0154272 A1 * | 7/2005 | Dirac et al. | 600/365 |
| 2005/0245795 A1 * | 11/2005 | Goode et al. | 600/302 |
| 2006/0134601 A1 * | 6/2006 | Torres et al. | 435/4 |
| 2006/0173252 A1 * | 8/2006 | Ellingsen et al. | 600/309 |
| 2008/0122431 A1 * | 5/2008 | Berkcan et al. | 324/126 |

* cited by examiner

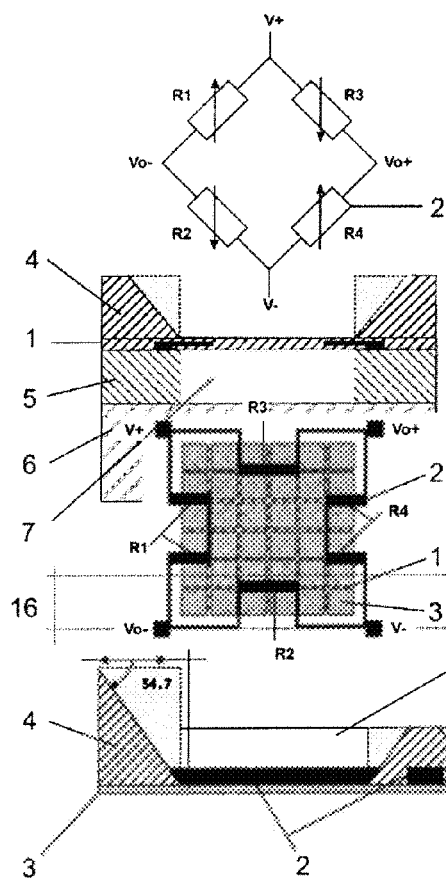
Fig. 2a
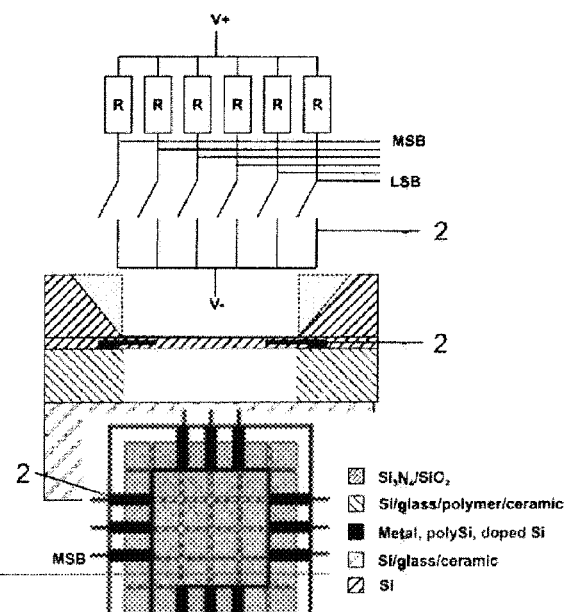
Fig. 2b
Fig. 2c

APPARATUS AND METHOD FOR MEASURING AUGMENTED OSMOTIC PRESSURE IN A REFERENCE CAVITY

This application is a national stage entry of International Application No. PCT/NO2008/000295, filed Aug. 20, 2008, designating the U.S., which claims the priority to Norwegian Patent Application No. 2007 4244, filed Aug. 20, 2007.

The present invention is related to an apparatus and method for measuring augmented osmotic pressure in a reference cavity bounded on one side by a semi-permeable membrane, and especially to an apparatus and method providing in vivo sensing of osmotic induced pressure gradients in the semi-permeable membrane, wherein the reference cavity and the membrane is encapsulated in a miniaturized device comprising transducers in operable contact with the semi-permeable membrane providing a measurement signal outputted from the device related to mechanical stress induced into the semi-permeable membrane or support structures of the semi-permeable membrane due to osmotic pressure changes in the reference chamber, according to the attached independent claim 1, and variants according to the depended claims 2 to 33.

There exists many proposed solutions in prior art for the problem of measuring osmotic pressure changes. For example, U.S. Pat. No. 4,538,616 by Robert Rogoff discloses a miniature implanted osmotic glucose sensor (a few millimeters in diameter and length) made of non-corrosive materials (plastic, silicone plastic, silver or stainless steel). The device is equipped with a single cellulose acetate semi-permeable membrane, and is directly implanted in a person's blood stream. The semi-permeable membrane encloses a single chamber filled with a standard osmotic solution (280-300 mOsml/L), and wherein the chamber is enclosed in the opposite end by a flexible impermeable diaphragm (thin plate of silicone or metal) equipped with an electrical connection. When the glucose concentration is below an acceptable level, the osmotic pressure of the blood is below the osmotic pressure of the standard osmotic solution inside the chamber, resulting in fluid flowing into the chamber and increasing the volume of the chamber. This causes the diaphragm to bulge outwards closing an electrical circuit outside the diaphragm, which activates an infusion device pumping glucose into the bloodstream. On the other hand, when the blood glucose concentration increase (above an acceptable level), a negative pressure inside the chamber is created, resulting in a bulging of the diaphragm in the opposite direction, which is closing a second electrical circuit, which activate pumping of insulin into the bloodstream.

U.S. Pat. No. 4,822,336 by John DiTraglia disclose a miniaturised implantable dual chamber device enclosed by two identical semi-permeable membranes permeable to glucoses but impermeable to larger molecules and body cells. Both chambers are equipped with pressure transducers (or optional $CO_2$ transducers) and are filled with isotonic suspensions with similar osmotic strength as the peritoneal liquid from which the device is indirectly measuring the blood glucose. One of the chambers is equipped with a suspension of yeast cells which produce $CO_2$ at a rate which varies according to the concentration of glucose in the blood, and which is translated into corresponding pressure changes by the generated $CO_2$. The second chamber acts as a controlling device subtracting any pressure induced signals (such as motion) that may affect both chambers. The device is further equipped with a thermostat regulated heater that maintains a temperature between 37 and 41° C. in order to optimise the $CO_2$ producing capabilities of yeast and hence improve the sensitivity and response time of the sensor.

U.S. Pat. No. 5,337,747 by Frederic Neftel, disclose a micro fabricated sensor that comprises two separate measuring devices located in parallel. Both make use of semi-permeable membranes where one device measures the osmotic pressure from all particles that are larger, including glucose, whereas the second measures the osmotic activity from all particles larger than glucose. The differential pressure measurement between these two assigns the contribution from glucose alone. Each device incorporates semi-permeable membranes that are integrated with a silicon support structure which maintains stability of the membrane. The membrane/support structure covers an internal (30 μm deep) measurement chamber comprising macromolecules maintaining a constant reference osmotic pressure. The measurement chamber is attached to a silicon pressure transducer, and where the membrane of the pressure transducer (20 μm thick) separates the measurement chamber from a 2nd chamber (20 μm deep airtight cavity of constant pressure) located on the inside face of the membrane belonging to the pressure transducer. The surface of the pressure transducer, reservoir and membrane is oxidised and attached together in a triple layer structure by a process referred to as "hot-bonding" at 1000° C. The semi-permeable membrane is covered by a layer of perfluorosulfonic acid (such as Nafion) which is biocompatible and hence suitable as an anti fouling agent for long term implantation.

U.S. Pat. No. 6,224,550 by Olav Ellingsen refers to a single osmotic sensor designed as a cylindrical device residing in the body and which communicates wirelessly with an external radio receiver mounted outside the body. Hence the device measures the absolute osmotic value of glucose through a single sensor. The device consist of a semi-permeable membrane (hollow fibre, sheet formed, corrugated) enclosed in a laser perforated titanium cylinder protecting the membrane from macromolecules or proteins formations (anti-bio fouling coating) as well as offering structural support. The cylinder contains an osmotic calibration solution that maintains equilibrium with the body osmotic pressure. A channel leads from the membrane cylinder system into the sensor housing in which the osmotic pressure in the calibration solution exerts force on a miniaturised spring loaded piston. The piston head acts as one face of a variable capacitor in which the second face is mounted on the opposite side of the cylinder containing the piston. Hence the capacitance is changed with the movements of the piston. The piston-capacitor system is connected to an inductor (antenna) to form a tuned LC oscillating circuit. The frequency of the transmitted signal will depend on the osmotic pressure in the device as a function of glucose or lactate.

The pressure transducer described in U.S. Pat. No. 6,224,550 require relative large fluxes of liquid through the semi-permeable membrane, since the actuator mechanism is based on volumetric changes caused by osmotic pressure, in contrast to direct iso-volumetric pressure measurements. This design requires large membrane areas which may provide inherent long response times. There is also an issue concerning friction forces between the movable/stationary piston and the cylinder. The design is not compatible with standard micro fabrication techniques that are preferably used to make small implantable units.

U.S. Pat. No. 6,268,161 by Han et al. presents a device that is similar to the vessel described in U.S. Pat. No. 4,538,616 but where the sensing device is based on a pH sensitive hydrogel occupying the chamber enclosed with a semi-permeable membrane in one end, and a pressure sensitive diaphragm in another end. The hydrogel alters its osmotic pressure in response to a pH changing by product, and hence expands/contracts in response to the presence of the by product. This in turn exerts a force on a pressure sensitive diaphragm, which alters the capacitance in a similar manner to that described in U.S. Pat. No. 5,337,747. The change in capacitance is being measured as a function of the concentration of glucose metabolised by an enzyme (glucose oxidase) embedded in the hydrogel.

The above identified prior art devices all comprises a separate pressure transducer embedded in the design, and which is kept separate at a distance from the osmotic membrane. The quality of the measurements provided by these devices and methods all assume that the osmotic membrane is completely stiff and rigid, and hence would direct all pressure/volume changes in the direction of the pressure transducer located for example at an opposite side of the membrane in a cavity bounded by the membrane, when the cavity is influenced by the osmotic process. However, a completely stiff or rigid membrane is difficult to manufacture. As known to a person skilled in the art, a semi-permeable membrane used in osmotic measurement apparatuses are provided with small holes allowing molecules below a certain size to pass the membrane. Therefore the stiffness of the membrane is difficult to maintain during pressure changes on one side of the membrane. There will always be a degree of flexibility in the membrane. The increase of pressure on one side of the membrane will always induce mechanical stress in the membrane, and in addition, any supporting structure in contact with the membrane may be influenced by the pressure changes on one side of the semi-permeable membrane. The stress induced into the structural elements of the membrane itself and/or supporting elements of the membrane may for example cause the semi-permeable membrane to bulge outward in a direction away from the cavity that the semi-permeable membrane is bounding, or the stress may provide a displacement of a supporting element relative to an other supporting element that is in operable contact with the membrane.

According to an aspect of the present invention, it is possible to measure stress induced effects on structural elements in the membrane itself or in supporting elements in contact with the semi-permeable membrane providing a consistent measurement of the osmotic pressure changes in a reference cavity bounded by the membrane. This allows omitting the prior art design comprising a separate pressure transducer, and instead integrate the pressure sensing elements into for example the support structure of the osmotic membrane, or the membrane itself, then any volume change inside the reference cavity bounded by the semi-permeable membrane due to pressure changes in the reference cavity would assert its effect on the membrane and/or support structure. This aspect of the present invention will provide a sensitive device, wherein a small volume change that occur inside the reference cavity, causes the reference cavity to become more isovolumetric in nature, and thus assert a higher force in response to a pressure change onto the membrane and/or support structure. Examples of embodiments of the sensor according to the present invention will provide fast response time for a given osmotic membrane architecture since a smaller volume change inside the reference cavity, consistent with the osmotic pressure changes, reduces the quantity of solvent required to diffuse into the cavity.

Further, according to yet another example of embodiment of the present invention, a membrane is arranged so as to reduce the diffusion barrier encountered by narrow pores/channels in order to provide a faster sensor. In addition, a method for filling and sealing off the enclosed reference cavity after the osmotic sensor components have been assembled, is also provided.

According to an example of embodiment of the present invention, the structure of the membrane is arranged such that one membrane may incorporate at least one transducer device located in the edge area of the membrane, or within the area occupied by the membrane. Another example of embodiment of the present invention is, to arrange the membrane as part of an array consisting of several membranes, each constituting at least one transducer device located in the edge area of the membrane, or within the area occupied by the membrane, in order to distribute the transducer device and to accommodate the thinnest possible membrane structure with maximum surface area.

According to an example of embodiment of the present invention, piezo resistive transducer elements are embedded in support structures, or a supporting frame of the semi-permeable membrane. The piezo resistive elements may be arranged in a Wheatstone bridge, or as at least one separate individual piezo resistive element. According to another example of embodiment of the present invention, a micromechanical switch device is arranged along edges of the semi-permeable membrane, wherein one pole of the switch element is arranged on the semi-permeable membrane itself, and another multi-pole is arranged on a surface of the supporting frame of the semi-permeable membrane such that when the semi-permeable membrane moves due to augmented osmotic pressure, more and more poles of the multi-pole arrangement is closed thereby indicating a measure of the actual osmotic pressure change inside the reference cavity. According to another example of embodiment of the present invention, capacitive elements containing alternating conductive and insulating layers are arranged along the edge of the semi-permeable membrane in such a manner that stress induced effects change the capacitance of the sensing elements and thereby indicating a measure of the actual osmotic pressure change inside the reference cavity. According to another example of embodiment of the present invention, a light source is incorporated into or in the proximity of the membrane in which any stress induced effects will change the intensity of the light reaching a detector, by incorporating an obstruction, such as for instance micropillars on the membrane, and which in turn would move into the path of the light as a result of augmented osmotic pressure inside the reference cavity. Yet another example of embodiment of the present invention is by directing the light onto the membrane, and measuring any changes in the direction of the reflected or refracted light in response to any stress induced effects changing the curvature gradient of the membrane.

According to an aspect of the present invention, a measuring apparatus comprises a micro chip device comprising a semi-permeable membrane, reference cavity and transducer elements, wherein circuitry transmits the transducer signals to a processing unit outside a patients body in which the micro chip device has been implanted, wherein the processing unit provides an indication of a medical status of the patient.

According to another example of embodiment of the present invention, the micro chip device comprises the processing unit, wherein circuitry of the micro chip device transmits signals indicating a medical status to a display unit outside a patient's body in which the micro chip device has been implanted.

According to another aspect of the present invention, a method of manufacturing a micro chip device comprises steps for filling the reference cavity with an osmotic active solution.

According to an aspect of the present invention, a semi-permeable membrane may be manufactured from an ultra thin sheet of silicon glass comprising pores with diameters in the range from 1 to 100 nm.

FIGS. 2a, 2b and 2c illustrates examples of embodiment of a device according to the present invention.

Figure 1:
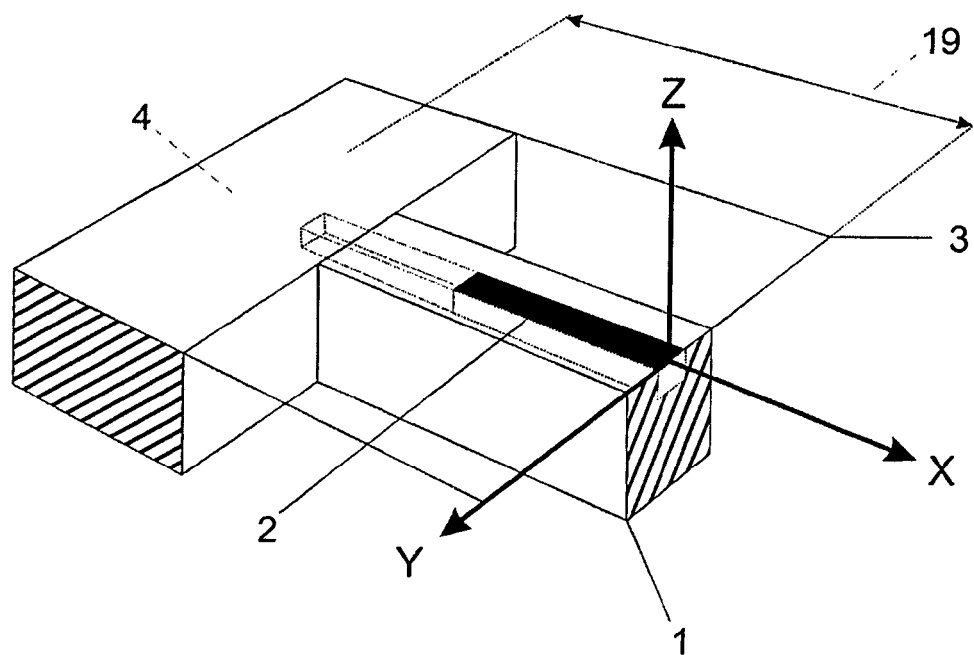
FIG. 1 illustrates an example of a transducer sensing element according to the present invention.

According to an aspect of the present invention, a pressure transducer comprising one or more sensing elements may be located in a supporting structure or supporting frame for the semi-permeable membrane, to the membrane itself. Preferably, these sensing elements are located along edges or in an area comprising edges of a semi-permeable membrane providing measurements of the osmotic trans-membrane pressure gradients across the semi-permeable membrane. The sensing elements of the transducer may be located in edges or areas close to edges of the semi-permeable membrane itself or in a support structure or supporting frame of the membrane. According to an example of embodiment of the present invention, the sensing elements are providing a suspension of the semi-permeable membrane above one side of a reference cavity. The FIGS. 2a, 2b, and 2c illustrates different examples of embodiments of devices according to the present invention comprising transducers in operable contact with the semi-permeable membrane such that the transducers are sensing any stress induced in the membrane due to an osmotic pressure change in the reference cavity bounded on one side by the membrane. The stress induced can be sensed by the transducers, for example when the augmented osmotic pressure in the reference cavity causes a transducer element to be compressed or stretched by the induced stress, or by a mechanical movement of the edges of the membrane when the membrane is displaced by the stress, for example when the stress is causing bending of the membrane and hence a displacement of edges of the membrane relative to the support structure or supporting frame of the membrane. Such devices, such as the examples of embodiments illustrated in FIGS. 2a, 2b and 2c of the present invention, may be manufactured as miniaturized micro chips suitable for insertion into a human body measuring for example glucose concentrations in blood vessels of a patient. The actual measurements performed are governed by the type of membrane used, for example the size of the pores of the semi-permeable membrane as known to a person skilled in the art. When the type of membrane is known the relationship between the measured osmotic pressure change and a specific solvent is known. Such in vivo measurements may require that the transducers are powered, and/or that signals can be transmitted out from the micro chip device when it is implanted into the body of a patient, for example, and received by a processing unit converting the measured osmotic pressure changes to medical information related to the patient's status.

According to an aspect of the present invention, a battery may be part of the micro chip device or the micro chip device may be powered by RF signals transmitted to the micro chip from a source outside the body of a patient implanted with the micro chip device according to the present invention. According to an example of embodiment of the present invention, signal processing is performed in processing circuitry being an integral part of the micro chip.

It is within the scope of the present invention to combine the measuring apparatus according to the present invention with any form of method and system for powering the micro chip devices when they are implanted into a body. It is also within the scope of the present invention to use any form of signal processing and/or transmission of measurement signals in and out of the implanted micro chip devices when such devices are implanted in a body.

FIG. 1 illustrates an example of a sensing element 2 in an edge area 19 of the membrane 3 in a support structure 1 (or in a supporting frame 4) comprised in an apparatus according to the present invention. The sensing elements 2 will be located in areas where the induced stress from an osmotic trans-membrane pressure gradient will inflict the largest relative rate of change of displacement or induced stress ($2^{nd}$ order derivative) in the support structure 1 (or supporting frame 4). Such areas are identified as the edge area 19 close to the supporting (silicon) frame 4. In the example depicted in FIG. 1, the sensing elements 2 are embedded into the surface of the support structure 1 of the semi-permeable membrane 3 arranged such that contact with the liquid environment surrounding the device is avoided. The support structure 1 may consist of silicon glass, epitaxial grown single crystalline silicon, poly silicon, amorphous silicon, bulk single crystalline silicon, a crystalline or polycrystalline or amorphous semiconductor material, ceramics, polymers or a combination thereof.

The sensing elements 2 may consist of either piezo resistive embedded doped p-type or n-type resistors in the single crystalline silicon support structure 1, or as deposited material in the form of polysilicon or metal. Doped silicon resistors exhibit a strain gauge factor that is more than one order of magnitude higher than that of metals, whereas metals exhibit lower temperature coefficients, offer higher temperature tolerances, and is more suitable if accurate resistances of the resistive elements are required. The piezo resistive elements 2 embedded in the membrane support structure 2 (or supporting frame 4) will exhibit resistive changes as an effect of compressive or tensile stress induced when the membrane support structure 1 moves in three dimensions (X, Y and Z directions as depicted in FIG. 1) in response to changing trans-membrane pressure gradients. In contrast, the sensing elements could also comprise an array of embedded micro electro mechanical (MEMS) switches which closes in turn as the membrane and the support structure is moving relative to each other in response to changing trans-membrane pressure gradients. The MEMS switches would act as a mechanical analogue to digital converter transforming a pressure change directly into a bit stream, or alternatively a series of discrete voltages or resistance changes depending on the applied bias circuitry. The resolution of the system would in this case be limited by the number of switches incorporated into each sensing element, and the number of sensing elements used. However, nano technology will provide a possibility to enhance the resolution of such MEMS arrangements. According to an example of embodiment of the present invention, a first pole of the MEMS switch is arranged on the membrane itself while a multi-pole configuration is arranged underneath the first pole FIGS. 2a and 2b are respective examples of embodiments of the present invention. FIG. 2a depicts an example of embodiment comprising piezo resistive sensing elements 2 arranged in a Wheatstone bridge arrangement. FIG. 2b depicts an example of embodiment comprising sensing elements 2 comprising MEMS switches as described above. In both examples of embodiment, the support structure 1 could be made of silicon (single crystalline or polycrystalline) or silicon glass (preferably $SiO_2$ or $Si_3N_4$), and be arranged to support the membrane, wherein the support is dependent on design constraints of the membrane 3. The membrane or support structure of the membrane can be manufactured by both anisotropic and isotropic etching technology resulting in walls of 54.7° and 90°, respectively, as known to a person skilled in the art. The semi-permeable membrane and support structure is made part of a supporting frame 4 of silicon which is attached to a rigid base substrate 5 of silicon, glass, ceramic or polymer, by a rigid spacer 6 made from one of the materials used in the base substrate 5. In some examples of embodiments the base substrate 5, spacer 6, is made from the same piece of material (see for example FIGS. 4 and 5, reference numeral 12). The base substrate 5, spacer 6, and the semi-permeable membrane/support structure enclose a hollow structure functioning as a reference cavity 7. The reference cavity 7 is filled with an (aqueous) osmotic active solution with an osmolality higher than the surrounding body fluids. Thus a positive osmotic pressure is maintained inside the reference cavity which prevents bubble formation (from a negative pressure) as well as ensuring that the semi-permeable membrane and the induced stress in the support structure and/or membrane is always spanned in one direction only.

In the example of embodiment depicted in FIG. 2a, the piezo resistive sensing elements 2 are configured as a Wheatstone bridge circuit, in which one pair (e.g. R1 and R4) is related to longitudinal stress component measurements (compressive stress), while the other pair (e.g. R2 and R3) is related to transverse stress component measurements (tensile stress). The differences in the longitudinal and transverse piezo resistance coefficients will then result in one pair increasing their resistance, whereas the second pair will decrease their resistance in response to a pressure change. Alternatively, the piezo resistive elements can be configured as either a single variable resistor or as two variable resistors, respectively. By providing a dimensionless measurement, (i.e. providing a measurement of an expression comprising resistive elements divided by another expression for the same resistive elements, as known to a person skilled in the art, this will cancel noise present in the nominator and denominator of the expression for the dimensionless measurement), for example white noise present in the measurements. The Wheatstone bridge is connected between two terminals V+ and V− as depicted in FIG. 2a providing for example a DC voltage across the bridge enabling the measurements of the resistive changes by measuring the output voltage at the terminals Vo+ and Vo−, as known to a person skilled in the art. In an example of embodiment of the present invention, an internally located battery or RF induced power from an externally located source powers the Wheatstone bridge. In another example of embodiment of the present invention, a pulsating signal is used to power the Wheatstone bridge, for example from the RF source powering the Wheatstone bridge. The measurements signals from the sensor can be processed in a phase lock (lock in) amplifier that will further cancel noise components and other surrounding RF signals from the measurement signals as known to a person skilled in the art. The output voltages Vo+ and Vo− can be transmitted wirelessly to an externally located processing unit providing further processing of the measurements, as known to a person skilled in the art.

In an other example of embodiment as depicted in FIG. 2b, the sensing elements 2 comprises MEMS switches arranged in a circuit wherein different respective switches are engages and are closing (or opening) the circuit with changing strain in the membrane and/or support structure as a response to a changing trans-membrane pressure gradient. The switches can for example be arranged as known to a person skilled in the art to form closed circuits resembling binary data conversion in which bit streams of highs (V+) and lows (V−) converts the pressure directly into digital data, omitting the use of sensor driver circuits and analogue to digital converters. In FIG. 2b there are illustrated output signals denoted MSB (most significant bit) to LSB (least significant bit). The switches can be manufactured using traditional MEMS fabrication technologies in which alternating electrically conducting layers or adjacent components are brought in or out of contact as the membrane moves back and forth. Future nanofabrication technologies may facilitate the integration of high density switching arrays to a great extent.

The sensor device according to the present invention will in its basic configuration measure absolute osmotic pressures. Only the passage through the semi-permeable membrane of the dissolved solute particles in question, for example glucose, will be retained by the semi permeable membrane disallowing components that have smaller physical sized particles than the dissolved solute particles in question to contribute to the total osmotic pressure changes. However, the concentration of sodium and chloride (major osmotic active particles) may increase under unusual circumstances such as severe dehydration of a human body. The concentration of urea may also increase under unusual circumstances such as acute or chronic kidney failure in a human body. However, since these particles belong to the class of particles that would pass through the semi-permeable membrane, the osmotic contribution from these particles under unusual circumstances should be excluded. The contribution from particles similar in size to the dissolved solute particles in question or larger will have to be considered, but can be neglected as long as these particles are low in numbers, are of relative constant concentration and does not change in a similar manner as the dissolved solute particles in question.

The reference cavity 7 will equilibrate to hydrostatic pressure changes occurring in the external environment due to solvent/water diffusing into the reference cavity 7 until there are no hydrostatic induced trans-membrane pressure gradients. The time used to reach equilibrium will be governed by the time constant of the sensor. Therefore, rapid hydrostatic pressure changes in the body may cause errors, for example, when a person stands up to walk/run after a period of rest, when a change of volume of the body tissue in which the sensor resides when flexing muscles or during physical or emotional stress, etc. occurs. Other circumstances are when rapid external atmospheric or hydrostatic pressure changes causes an effect on the hydrostatic pressure inside the body of a person, for example, when a person is a passenger in an airplane that are changing altitude rapidly such as during take off and landing, when a person is sky diving or base jumping, when a person is diving. If the external pressure changes are slower than the time constant of the sensor, there will be no errors due to hydrostatic pressure changes in the body of the person. For example when walking at steady rate, air flights at constant altitude, transition from low to high pressure in the weather pattern, and diving at a steady/constant depth.

Figure 3:
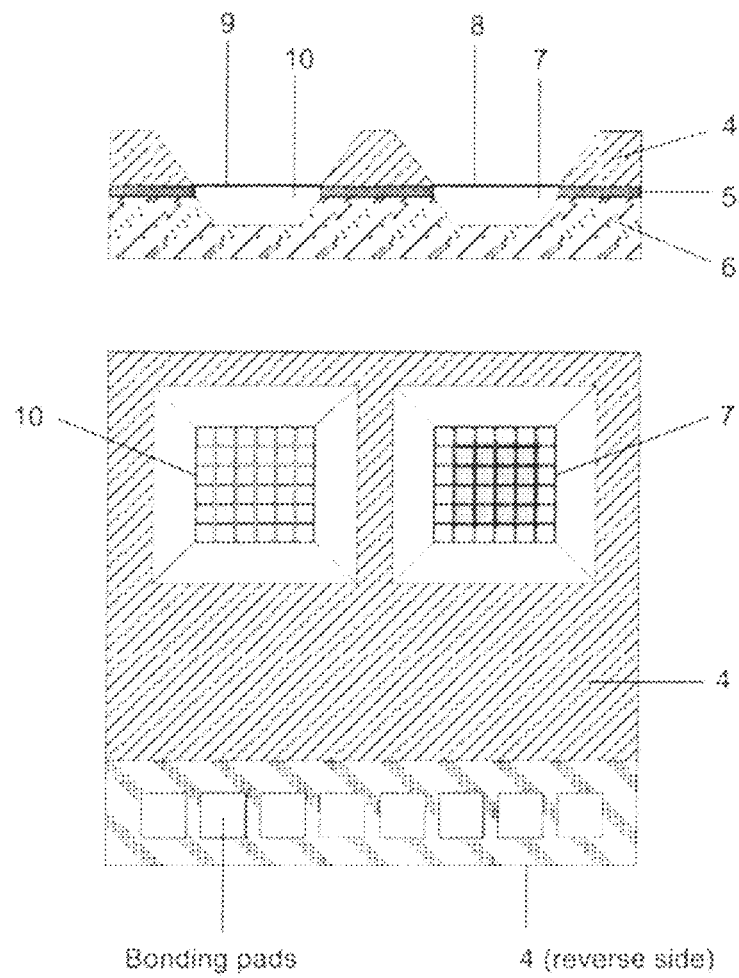
FIG. 3 illustrates an example of an osmotic membrane and support structure according to the present invention.

According to another aspect of the present invention, measurement problems related to the time constant of the micro chip device may be mitigated by providing differential measurements in stead of absolute measurements by using two reference chambers, 7 and 10, according to the present invention in an arrangement as depicted for example in FIG. 3. A first pressure transducer is integrated into the support structure of a semi-permeable membrane measuring both osmotic induced and rapid hydrostatic induced trans-membrane pressure gradients 8 in the reference chamber 7, whereas the second transducer is integrated into the support structure of a solid membrane measuring only absolute hydrostatic pressure 9 in reference cavity 10. The reference cavity 10 is sealed under vacuum or under a constant pressure and maintains the vacuum or constant pressure throughout the lifetime of the device. In this embodiment, the rapid hydrostatic pressure can be eliminated from the measurements as known to a person skilled in the art.

Figure 4:
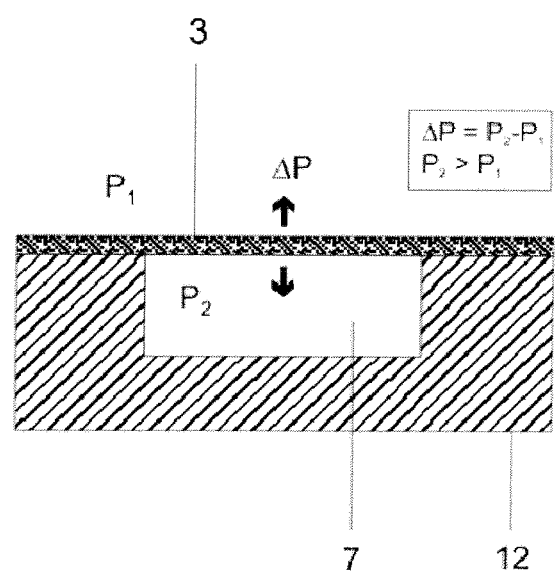
FIG. 4 illustrates some functional principles according to examples of embodiments of the present invention.

FIG. 4 illustrates the functional principles of a reference cavity 7 according to the present invention. The reference cavity 7 is bounded on all sides but one of a rigid material 12 maintaining zero expansion in these directions independent of any pressure changes that are generated within the reference cavity 7. The last side of the reference cavity 7 is enclosed by the membrane 3. This ensures that the only volume changes seen in the reference cavity 7 in response to generated pressure differences will move in the direction of the membrane 3. Hence, only the membrane 3 will be subject to any pressure differences between the reference cavity 7 and the exterior of the device, and hence be able to perform measurements of corresponding trans-membrane pressure gradients.

Figure 5:
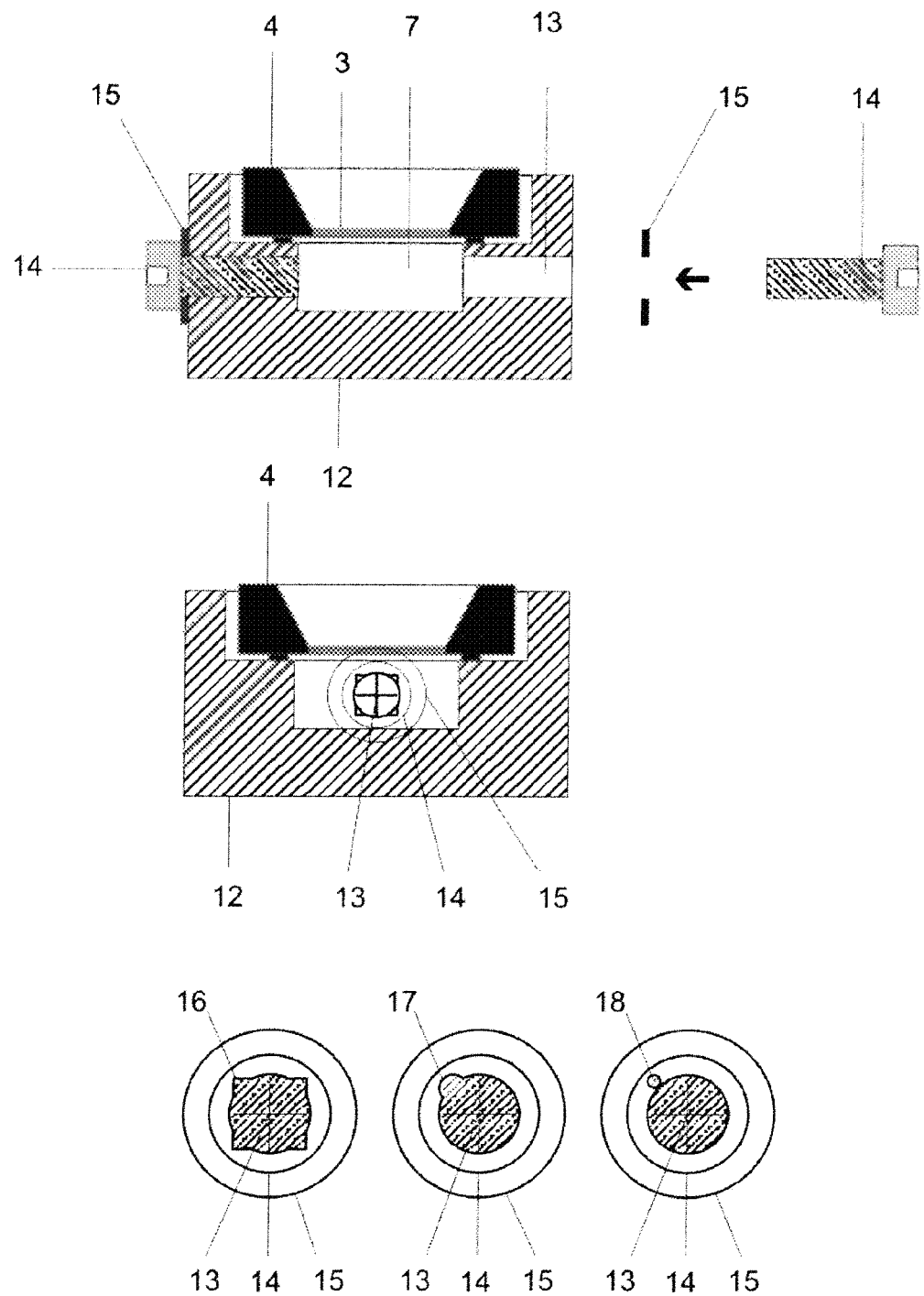
FIG. 5 illustrates method steps for filling and sealing the internal reference cavity according to an example of embodiment of the present invention.

According to an aspect of the present invention, a reference cavity bounded on one side by the membrane must be filled with an appropriate osmotic active solution and be sealed after assembly of the micro chip device according to the present invention. FIG. 5 illustrates the filling and sealing method of an internal reference cavity 7. The reference cavity 7 is bounded by the pressure transducer chip 4 comprising the semi-permeable membrane, support structure and sensing elements, and the rigid base substrate material 12. Two access channels 13 are arranged in the base substrate 12 which permits external access to the reference cavity 7. One of the two channels are used to fill the reference cavity 7 with an (aqueous) osmotic active solution with an osmolality higher than that of the surrounding body fluids by the aid of a glass capillary and micro injector, as known to a person skilled in the art. The second channel acts as an expansion relief by which trapped air can escape as the air is expelled from the cavity by the injected fluid. Once the reference cavity has been completely filled with the osmotic solution, the capillary is removed and a first (e.g. watch hairspring stud) screw 14 is attached sealing the second channel with a miniature gasket 15 attached to the screw 14. The same procedure is then repeated with a second screw 14 and gasket 15 sealing off the first channel 13. In contrast, fastening the second screw would normally provide an increase of the absolute volume of the reference cavity 7 by pushing the osmotic solution present in the channel 13 towards the interior of the cavity 7 as the screw is turned. This could cause the pressure inside the cavity to exceed the pressure tolerance of the membrane, and thereby damage the membrane. In order to prevent this to happen, an example of embodiment of the device according to the present invention comprises holes in the threads of the screws 14, denoted pressure relief channels 16 which permits efflux of osmotic fluid as the screw is tightened. The pressure relief channel 16 can be made as a square access channel in the base substrate material 12 in which threads are made to fit the screw. The corners of the square access channel 16 then acts as the pressure relief channels 16. Alternatively, if the threads are made directly in the base material 12 without a square access channel, a single pressure relief channel 17 could be drilled located in the circumference of the threads together with the alignment hole of the threads prior to the threads being made. Alternatively, if the threads of the screws are moulded, pressure relief channels 18 could be made by attaching a small wire to the screw threads prior to moulding. The wire could then be removed with or after the screw has been removed. The pressure relief channel is sealed off by the aid of the miniature gasket 15 as disclosed above. Alternatively, a single screw and pressure relief channel could be used if the capillary filling the reference cavity can be inserted far enough into the cavity to expel excess air out through the single access channel in which the capillary is used. Alternatively, a miniaturised bolt structure penetrating both access channels and equipped with an external nut could be implemented, hence bypassing the need of pressure relief channels by pushing out the excess fluid as the bolt is inserted through the two access channels 13 prior to sealing.

When the filling and sealing of the reference cavity is complete, the device may be stored in an isotonic solution to prevent evaporative losses of reference fluid through the semi-permeable membrane prior to use.

The (aqueous) osmotic active solution with an osmolality higher than the surrounding body fluids are denoted the reference fluid. A positive osmotic pressure is maintained inside the reference cavity which prevents bubble formation as well as ensuring that the semi-permeable membrane and the induced stress in the support structure always is spanned in one direction only. The reference fluid consists of an aqueous solvent with a composition similar to the body fluid, and in which most of the dissolved particles may diffuse through the membrane and thus equilibrate the reference fluid with the surrounding body fluids. Further, the fluid contains additional macro particles that are impermeable to the semi-permeable membrane and which increase the osmolality of the reference solution above that of the body fluids. These macro particles will be present at a constant concentration and thus maintain a positive reference osmotic pressure which is independent of the movement of smaller osmotic active components through the membrane. However, the reference osmotic pressure will follow the baseline movement in pressure caused by the movement of smaller dissolved components, and hence it is important to ensure that the sensor neutralises the effect of these smaller dissolved components. According to an aspect of the present invention, a semi-permeable membrane may be manufactured from an ultra thin sheet of silicon glass comprising pores with diameters in the range from 1 to 100 nm.

The sensor should be made from biocompatible and non toxic materials. However inherent biocompatible materials may induce a certain degree of thrombosis (blood coagulation). Non-thrombogenic materials are defined as those that do not enhance protein binding or activate platelets or white cells. Hence stainless steel (screws), glass, ceramics (base material) and (silicon) glass surfaces (membrane) may require a non-thrombogenic coating. Only silicone plastic in terms of polyethylene glycol/oxide (PEG/PEO), polyvinylpyrrolidone (PVP) can be rendered haemocompatible today. According to an aspect of the present invention, the use of biocompatible materials such as polyurethane, polyanhydrides and polyacetates in addition to titanium as the sensor enclosure is possible.

A semi-permeable membrane according to the present invention may be manufactured in one monolithic unit. Diffusion in small pores will deviate from Fick's first law, thus reducing the diffusion coefficient through the membrane compared to that of free media. Information about transfer speed will be used in the design constraints to estimate the pore size, minimum porosity, surface area and reference chamber volume required to meet the desired response time and required trans-membrane pressure gradients. The manufacture of a specific micro chip device would be based on one or more of the following evaluations:

a) Estimation of the physical strength with respect to the material, surface area, thickness and porosity. Calculations with respect to the support structure and membrane elements dimensions and geometry focusing on stress analysis with respect to trans-membrane osmotic pressure changes over a specified dynamic range. One aim is to identify the optimal membrane or support structure that can be realised with respect to area, material and process technology.

b) Choice of process technology related to silicon micromachining, CMOS or nanotechnology.

c) Definition of the membrane or support structure. Integration of sensing elements into the membrane or support structure beams. This could be achieved by modifying the material by ion implantation or by metal or polysilicon deposition defining local conducting regions exhibiting piezo resistive behaviour. Alternatively the integration of MEMS switches for digital data conversion.

d) Deposition of encapsulation layer for electrical insulation and chemical protection. The encapsulation layer could comprise a part of the semi-permeable membrane.

e) Definition of pores in the membrane by standard lithographic techniques (photolithography or e-beam lithography), reactive ion etching, molecular beam epitaxy and or nanotechnology based on molecular self organisation such as block copolymer lithography.

f) Release of the membrane and support structure with the aid of wet chemical etching process, electrochemical etching processes, or dry chemical etching processes such as deep reactive ion etching.

g) Making the pores hydrophilic by chemical modification.

h) Encapsulation in a biocompatible polymer.

An example of embodiment of the present invention is a microchip device in which a generic array of membranes are designed from a bulk single crystalline silicon wafer and which should resist a trans-membrane pressure gradient of 1 bar. Each membrane consists of silicon glass and measures approximately 5 by 5 µm in extent and is 50 nm thick, being arranged in a rectangular array of 80 by 80 membranes, each separated by rectangular support beams, which are approximately 7 µm wide and 20 µm thick. The whole array consists of 6400 membranes and covers an area of approximately 1 by 1 mm. Each membrane is made porous by nanometer sized pores ranging from 1 to 100 nm in diameter and arranged such as to occupy an area of $4/10$ of the surface area of the membrane. Given that each membrane has a porosity of say 40%, then the effective porosity of the array is determined to approximately 6.5%. An embodiment could be subject to structural changes due to evaluations done in subsequent iterations, such as array geometry, membrane size, membrane thickness, support structure thickness, support structure width, porosity and material composition, etc.

According to an aspect of the present invention, the micro chip device may be manufactured as a disposable device. According to another aspect of the present invention, micro chip devices according to the present invention are shipped in containers comprising an isotonic solution.

The invention claimed is:

1. Apparatus for measuring augmented osmotic pressure in a reference cavity filled with an osmotic active solution, wherein the reference cavity is bounded on one side by an attached semi-permeable membrane coupled with at least one transducer device operable therewith, the at least one transducer device is capable of sensing any mechanical induced bulging in the semi-permeable membrane due to augmented osmotic pressure in the reference cavity, and providing a sensing measurement output consistent with the amount of augmented osmotic pressure, wherein at least one sensing element of the transducer device(s) is located along edges of the semi-permeable membrane.

2. Apparatus according to claim 1, wherein the at least one transducer device is arranged to sense induced mechanical stress in support structures or a supporting frame of the semi-permeable membrane, wherein the induced mechanical stress in the support structures or the supporting frame is mechanically transferred from the semi-permeable membrane when there is an augmentation in the osmotic pressure in the reference cavity.

3. Apparatus according to claim 2, wherein the at least one transducer device is embedded into the support structures or the supporting frame.

4. Apparatus according to claim 3, wherein the at least one transducer device comprises piezo resistive elements.

5. Apparatus according to claim 4, wherein the piezo resistive elements are arranged as a Wheatstone bridge.

6. Apparatus according to claim 5, wherein the piezo resistive elements are arranged as independent sensing elements.

7. Apparatus according to claim 3, wherein the at least one transducer element comprises at least one piezo resistive element.

8. Apparatus according to claim 3, wherein the at least one transducer element is arranged as micro electro mechanical (MEMS) switches.

9. Apparatus according to claim 3, wherein the at least one transducer element is arranged as variable capacitive elements.

10. Apparatus according to claim 1, wherein the apparatus is powered by an embedded battery.

11. Apparatus according to claim 1, wherein the apparatus is powered by radio frequency (RF) signals from an RF source outside the apparatus.

12. Apparatus according to claim 11, wherein the RF signal powering the apparatus is pulsed such that the sensing measurement output consistent with the amount of augmented osmotic pressure is transmitted as a pulsed RF signal.

13. Apparatus according to claim 12, wherein the pulsed measurement signal is received by a phase lock in amplifier located outside the apparatus.

14. Apparatus according to claim 1, wherein the sensing measurement output consistent with the amount of augmented osmotic pressure is processed by a unit located outside the apparatus.

15. Apparatus according to claim 14, wherein the unit processing measurement signals is embedded in the apparatus.

16. Apparatus according to claim 14, wherein the processing unit converts the measurement signals to an indication of a medical status of a patient implanted with the apparatus.

17. Apparatus according to claim 15, wherein the transmitted output signal is received by a display unit located outside the apparatus displaying a medical status of a patient implanted with the apparatus.

18. Apparatus according to claim 14, wherein the processing unit provides a processing of the measurement signals according to pore size of the semi-permeable membrane.

19. Apparatus according to claim 1, wherein the sensing measurement output consistent with the amount of augmented osmotic pressure is transmitted as a dimensionless measurement signal.

20. Apparatus according to claim 3, wherein the at least one transducer device comprises piezo resistive elements embedded as doped p-type or n-type resistors in a single silicon crystalline support structure.

21. Apparatus according to claim 20, wherein the piezo resistive elements are deposited as poly silicon or metal on the support structure.

22. Apparatus according to claim 1, wherein the osmotic active solution in the reference cavity has a higher osmolality than the fluids that the apparatus is intended to be used with for measurements.

23. Apparatus according to claim 1, wherein the apparatus comprises two respective reference cavities, wherein one of the cavities is used with a solid membrane measuring only rapid hydrostatic induced trans-membrane pressure gradients, and the sensing measurement output signal is subtracted with the measured rapid hydrostatic contribution.

24. Apparatus according to claim 1, wherein the reference cavity is arranged with a first channel for inserting a micro injector inserting an osmotic active solution into the reference cavity, and a second channels acting as an expansion relief when filling the reference cavity, and wherein the channels are sealed off with screws after the filling is complete, wherein one of the screws are arranged with pressure relief channels.

25. Apparatus according to claim 24, wherein the pressure relief channels are provided by letting at least one of the first or second channels comprise a square channel profile.

26. Apparatus according to claim 1, wherein the apparatus is manufactured as a disposable device.

27. Apparatus according to claim 1, wherein the apparatus is shipped in a container comprising an isotonic solution.

28. Apparatus according to claim 1, wherein the apparatus is embedded as a micro chip device.

29. Apparatus according to claim 2, wherein the support structure of the semi-permeable membrane is manufactured from one of the materials in the list comprising silicon glass, poly silicon, amorphous silicon, epitaxial grown silicon, bulk single crystalline silicon, crystalline or amorphous or poly-crystalline semiconductor, ceramics and polymers.

30. Apparatus according to claim 1, wherein the semi-permeable membrane is arranged as part of an array of several membranes, each constituting at least one transducer device operable therewith.

31. Apparatus for measuring augmented osmotic pressure in a reference cavity filled with an osmotic active solution, wherein the reference cavity is bounded on one side by an attached semi-permeable membrane coupled with at least one transducer device operable therewith, the at least one transducer device is capable of sensing any mechanical induced bulging in the semi-permeable membrane due to augmented osmotic pressure in the reference cavity, and providing a sensing measurement output consistent with the amount of augmented osmotic pressure, wherein at least one sensing element of the transducer device(s) is located in areas where the induced stress from an osmotic trans-membrane pressure gradient will inflict the largest relative rate of change of displacement or induced stress in a support structure or supporting frame of the semi-permeable membrane.

* * * * *